US007963940B2

(12) United States Patent
Holman et al.

(10) Patent No.: US 7,963,940 B2
(45) Date of Patent: Jun. 21, 2011

(54) LOCAL PERFUSION DEVICE

(75) Inventors: Thomas J. Holman, Princeton, MN (US); Jan Weber, Maple Grove, MN (US); Tracee Eidenschink, Wayzata, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1703 days.

(21) Appl. No.: 11/208,879

(22) Filed: Aug. 22, 2005

(65) Prior Publication Data

US 2007/0060918 A1 Mar. 15, 2007

(51) Int. Cl.
*A61M 29/00* (2006.01)
(52) U.S. Cl. .................................... 604/96.01
(58) Field of Classification Search .............. 607/105; 606/21; 604/101.04, 96.01
See application file for complete search history.

(56) References Cited

U.S. PATENT DOCUMENTS

| | | |
|---|---|---|
| 3,859,986 A | 1/1975 | Okada et al. |
| 3,913,581 A | 10/1975 | Ritson et al. |
| 4,278,090 A | 7/1981 | van Gerven |
| 4,423,725 A | 1/1984 | Baran et al. |
| 4,531,935 A | 7/1985 | Berryessa |
| 4,581,017 A | 4/1986 | Sahota |
| 4,860,744 A | 8/1989 | Johnson et al. |
| 4,946,460 A | 8/1990 | Merry et al. |
| 5,041,093 A | 8/1991 | Chu |
| 5,078,713 A | 1/1992 | Varney |
| 5,147,355 A | 9/1992 | Friedman et al. |
| 5,759,182 A | 6/1998 | Varney et al. |
| 5,775,338 A | 7/1998 | Hastings |
| 5,799,661 A | 9/1998 | Boyd et al. |
| 5,837,003 A | 11/1998 | Ginsburg |
| 5,846,238 A | 12/1998 | Jackson et al. |
| 5,861,021 A | 1/1999 | Thome et al. |
| 5,868,735 A | 2/1999 | Lafontaine |
| 5,902,299 A | 5/1999 | Jayaraman |
| 5,910,104 A | 6/1999 | Dobak, III et al. |
| 5,957,963 A | 9/1999 | Dobak, III |
| 5,971,979 A | 10/1999 | Joye et al. |
| 5,976,119 A | 11/1999 | Spears et al. |
| 6,033,383 A | 3/2000 | Ginsburg |

(Continued)

FOREIGN PATENT DOCUMENTS

WO WO 97/06739 2/1997

(Continued)

OTHER PUBLICATIONS

Wakida et al., "Percutaneous Cooling of Ischemic Myocardium by Hypothermic Retroperfusion of Autologous Arterial Blood: Effects on Regional Myocardial Temperature Distribution and Infarct Size," *J. Am. Coll. Cardiol.*, 1991, 18(1):293-300.

(Continued)

*Primary Examiner* — Kevin C Sirmons
*Assistant Examiner* — Deanna K Hall
(74) *Attorney, Agent, or Firm* — Seager, Tufte & Wickhem, LLC

(57) ABSTRACT

A device for providing a fluid to a target tissue region of a body vessel is described. The device includes an elongate member having a lumen to receive a fluid, and a structure deployable from a distal portion of the elongate member to channel blood flowing in the vessel. Also described are a method of, and a system for, providing a fluid to a target tissue region inside a body.

19 Claims, 7 Drawing Sheets

U.S. PATENT DOCUMENTS

| | | |
|---|---|---|
| 6,042,559 A | 3/2000 | Dobak, III |
| 6,051,019 A | 4/2000 | Dobak, III |
| 6,056,743 A | 5/2000 | Ellis et al. |
| 6,063,082 A | 5/2000 | DeVore et al. |
| 6,126,684 A | 10/2000 | Gobin et al. |
| 6,146,411 A | 11/2000 | Noda et al. |
| 6,206,004 B1 | 3/2001 | Schmidt et al. |
| 6,241,722 B1 | 6/2001 | Dobak et al. |
| 6,283,959 B1 | 9/2001 | Lalonde et al. |
| 6,290,696 B1 | 9/2001 | Lafontaine |
| 6,355,029 B1 | 3/2002 | Joye et al. |
| 6,409,747 B1 | 6/2002 | Gobin et al. |
| 6,428,534 B1 | 8/2002 | Joye et al. |
| 6,432,124 B1 | 8/2002 | Worthen et al. |
| 6,468,268 B1 | 10/2002 | Abboud et al. |
| 6,481,439 B1 | 11/2002 | Lewis et al. |
| 6,502,576 B1 | 1/2003 | Lesh |
| 6,514,245 B1 | 2/2003 | Williams et al. |
| 6,517,533 B1 | 2/2003 | Swaminathan |
| 6,530,234 B1 | 3/2003 | Dobak, III et al. |
| 6,540,740 B2 | 4/2003 | Lehmann et al. |
| 6,558,412 B2 | 5/2003 | Dobak, III |
| 6,575,966 B2 | 6/2003 | Lane et al. |
| 6,589,234 B2 | 7/2003 | Lalonde et al. |
| 6,589,264 B1 * | 7/2003 | Barbut et al. ............... 606/200 |
| 6,620,188 B1 | 9/2003 | Ginsburg et al. |
| 6,635,068 B1 | 10/2003 | Dubrul et al. |
| 2001/0005791 A1 | 6/2001 | Ginsburg et al. |
| 2001/0016725 A1 | 8/2001 | Valley et al. |
| 2001/0025175 A1 | 9/2001 | Panescu et al. |
| 2001/0027333 A1 | 10/2001 | Schwartz |
| 2002/0010460 A1 | 1/2002 | Joye et al. |
| 2002/0029073 A1 | 3/2002 | Schwartz |
| 2002/0032438 A1 | 3/2002 | Lafontaine |
| 2002/0045892 A1 | 4/2002 | Kramer |
| 2002/0045894 A1 | 4/2002 | Joye et al. |
| 2002/0056460 A1 | 5/2002 | Boyd et al. |
| 2002/0111616 A1 | 8/2002 | Machold et al. |
| 2002/0161351 A1 | 10/2002 | Samson et al. |
| 2003/0060762 A1 | 3/2003 | Zvuloni et al. |
| 2004/0030259 A1 | 2/2004 | Dae et al. |
| 2004/0267338 A1 * | 12/2004 | Harrison ............... 607/105 |

FOREIGN PATENT DOCUMENTS

| | | |
|---|---|---|
| WO | WO 00/69323 | 11/2000 |
| WO | WO 01/36035 | 5/2001 |
| WO | WO 01/60441 | 8/2001 |
| WO | WO 02/58605 | 8/2002 |

OTHER PUBLICATIONS

Hale et al., "Regional Hypothermia Reduces Myocardial Necrosis Even When Instituted After the Onset of Ischemia," *Basic Research in Cardiology*, 1997, 92(5):351-357.

Dave et al., "Hypothermic, Closed Circuit Pericardioperfusion: A Potential Cardioprotective Technique in Acute Regional Ischemia," *J. Am. Coll. Cardiol.*, 1998, 13(7):1667-1671.

Schwartz et al., "Regional Topical Hypothermia of the Beating Heart: Preservation of Function and Tissue," *The Annals of Thoracic Surgery*, 2001, 72(3):804-809.

Dixon et al., "Acute Myocardial Infarction," *Oral Abstracts*, 2001, p. 78.

http://aha.agora.com/abstractviewer/av_print.asp—Hoek, et al., "Do We Reperfuse or Cool Down First to Resuscitate Ischemic Tissue?," printed from the Internet on Sep. 3, 2002, 1 page.

http://www.inbthermoelectric.com/index.html—INB Products, printed from the Internet on Nov. 25, 2002, 5 pages.

* cited by examiner

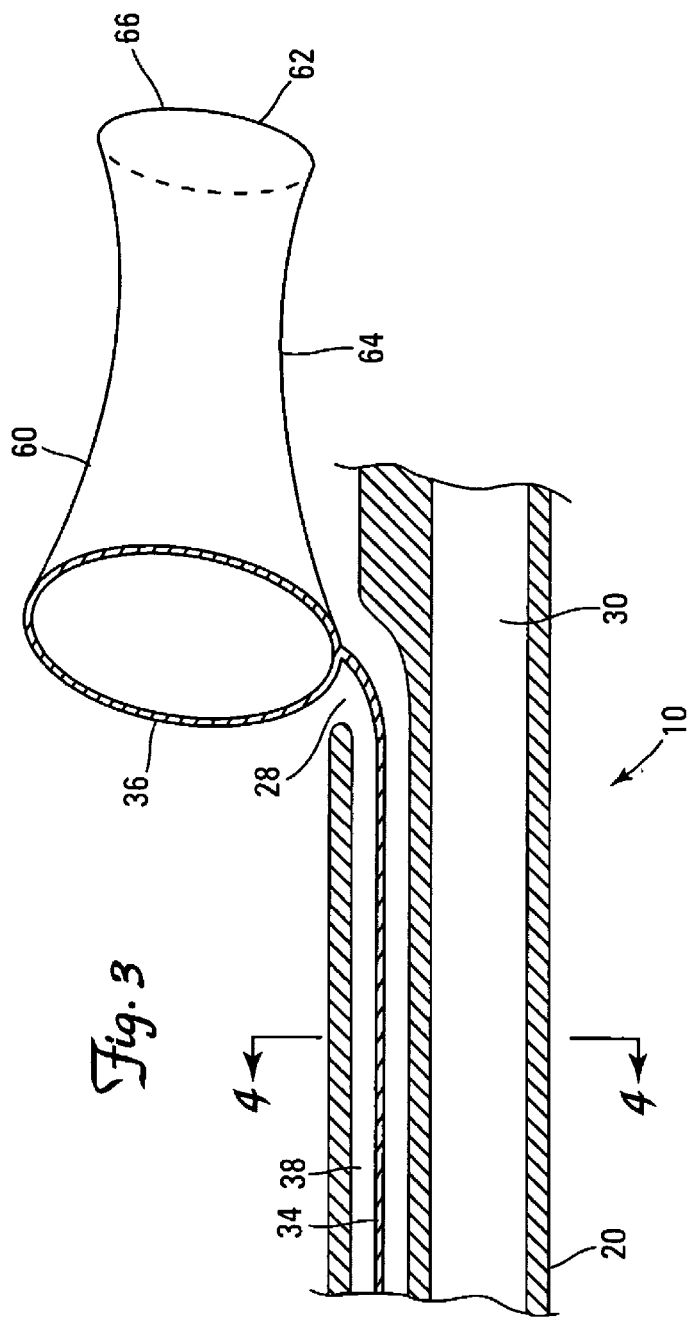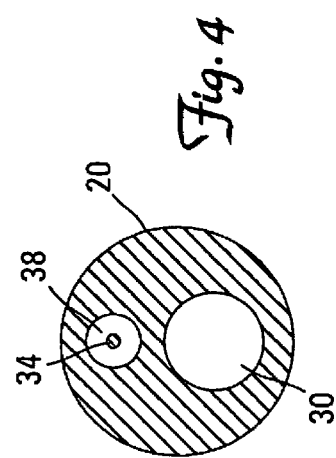

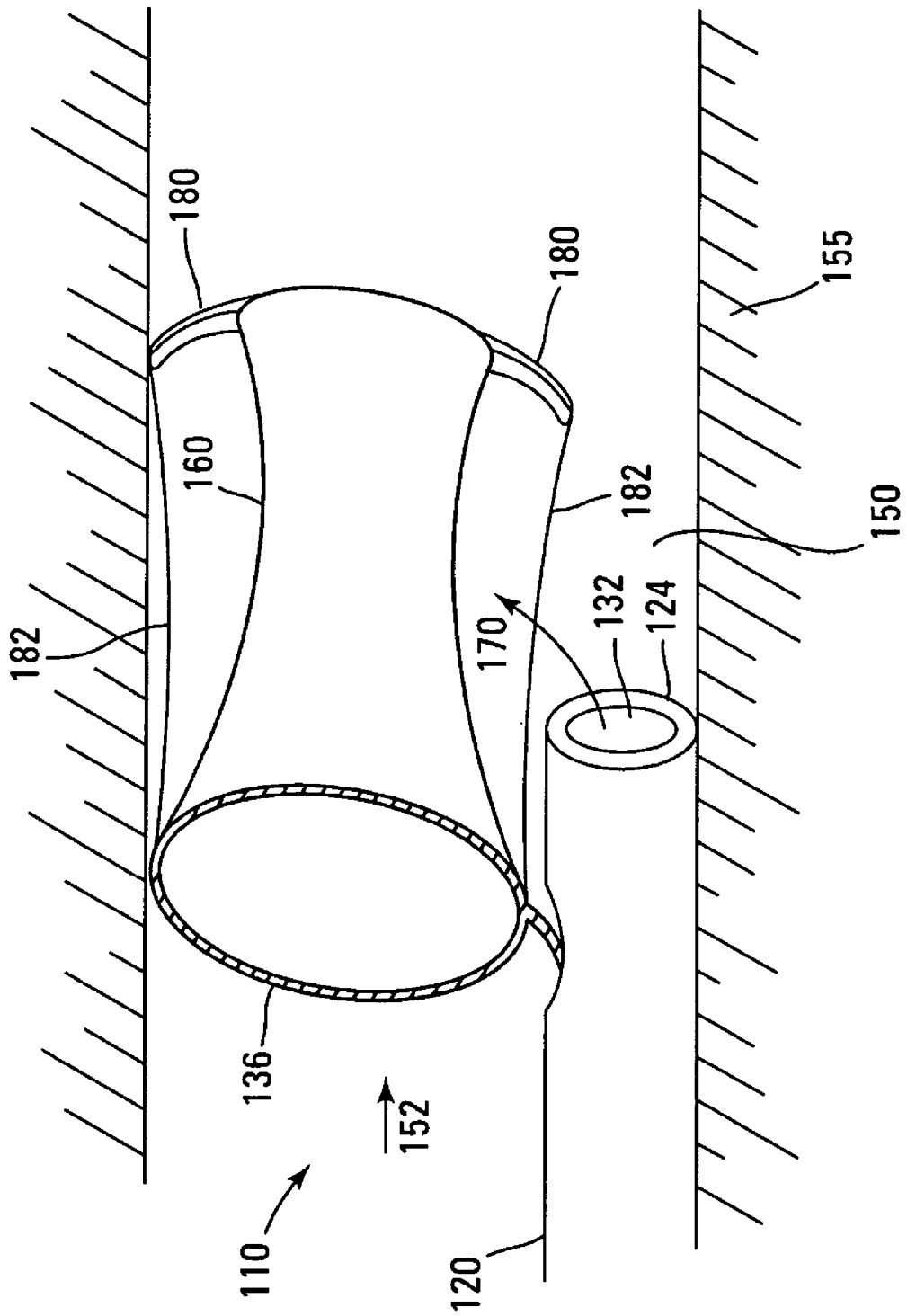

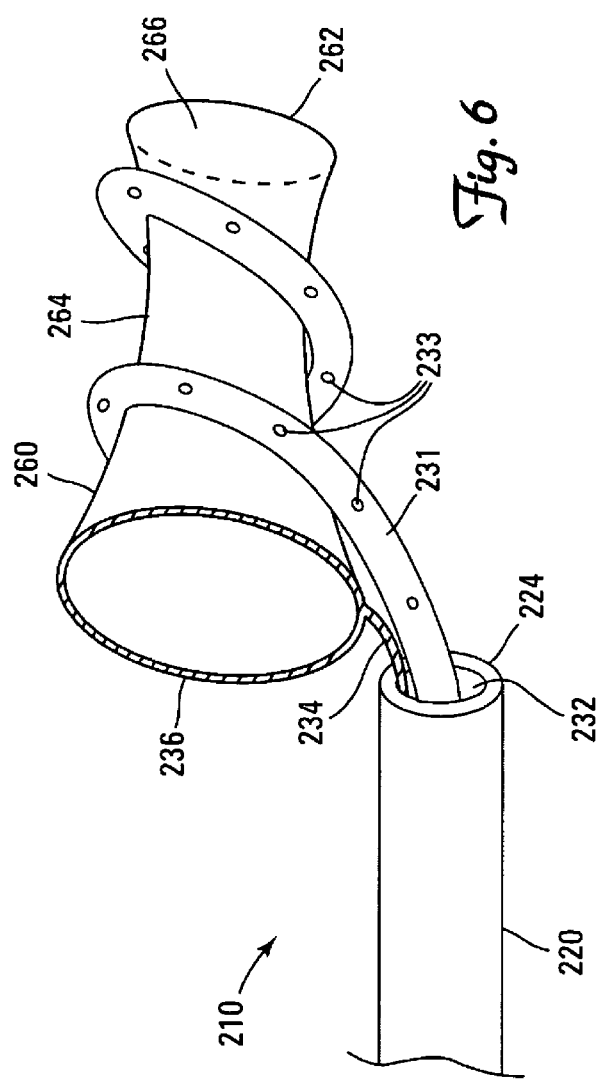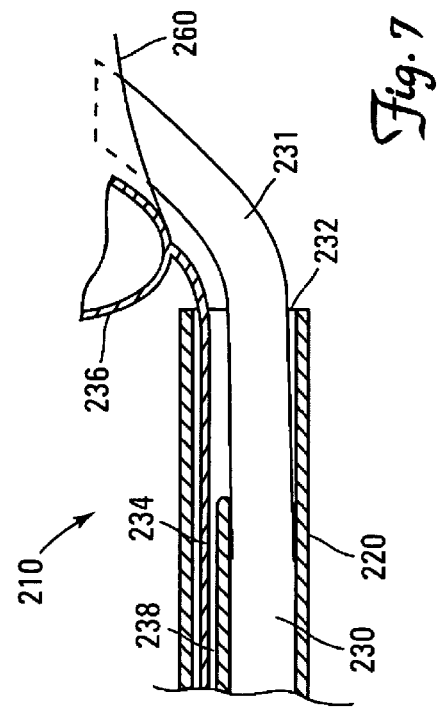

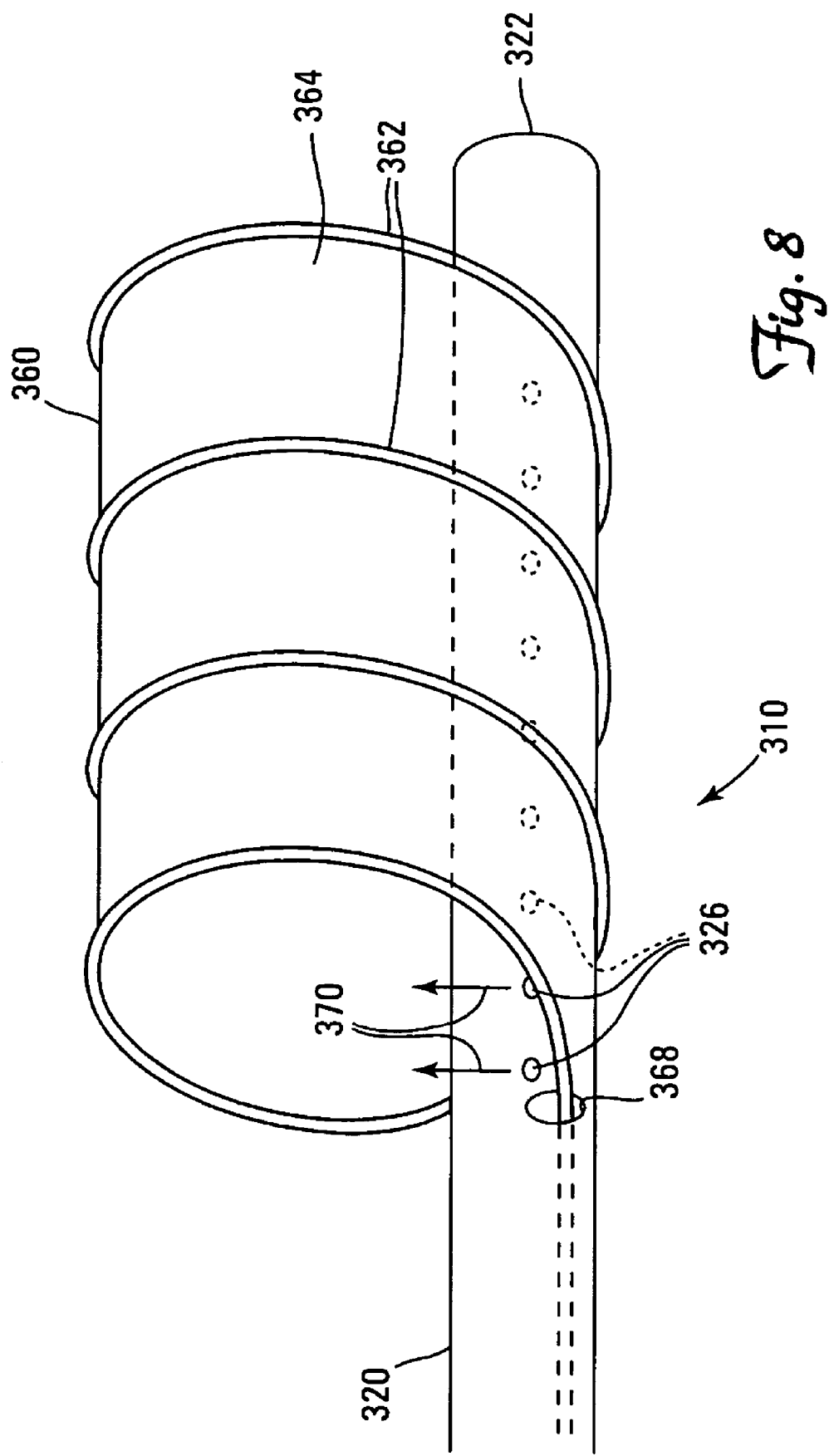

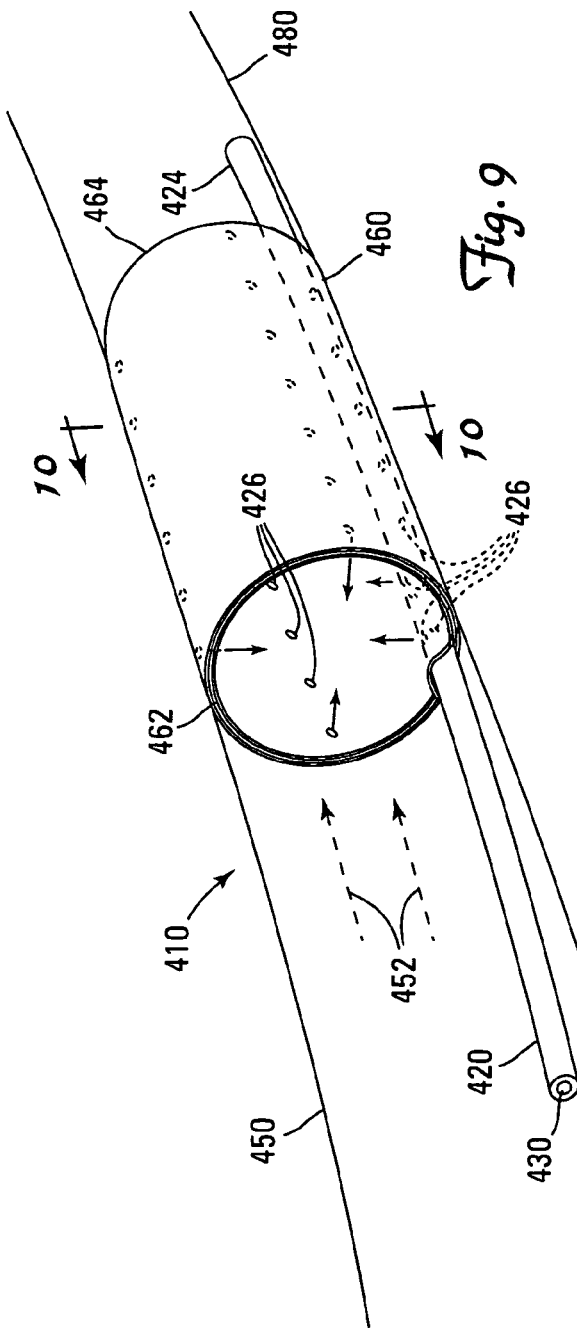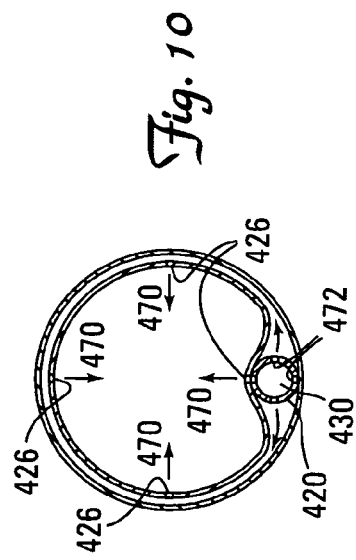

LOCAL PERFUSION DEVICE

TECHNICAL FIELD

This invention relates to medical devices, and more particularly to local cooling devices.

BACKGROUND

Myocardial ischemia, and in severe cases acute myocardial infarction (AMI), can occur when there is inadequate blood circulation to the myocardium due to coronary artery disease. Evidence suggests that early reperfusion of blood into the heart, after removing a blockage to blood flow, reduces damage to the myocardium. However, the reestablishment of blood flow into the heart may cause a reperfusion injury to occur. Reperfusion injury is believed to be due to the build up of waste products on the myocardium during the time blood flow was inadequate and the reaction of these waste products with oxygen in the blood when normal blood flow is reestablished. It is possible to reduce reperfusion injury to the myocardium by cooling the myocardial tissue prior to reperfusion. Mild cooling of the myocardial tissue to a temperature between 28 and 36 degrees Celsius provides a protective effect, likely by the reduction in the rate of chemical reactions and the reduction of tissue activity and associated metabolic demands.

Local cooling is a site specific, temperature-reducing procedure that affects the cascade of events controlling the future health of the arterial wall that was recently damaged by a blockage in the blood stream. Emergency room procedures may include post-angioplasty local cooling of the lesion site. This additional procedure after dilating the lesion and re-opening the vessel is beneficial because clinical data has also shown that cooling the arterial wall just after angioplasty reduces restenosis or re-clogging of the artery. These outcomes can affect the long-term cost of treating the patient. However, short-term costs and ease of use are also important considerations.

Current technologies utilized in local cooling procedures vary widely. One method of cooling myocardial tissue is to place an ice pack over the patient's heart. Another method involves puncturing the pericardium and providing cooled fluid to a reservoir inserted into the pericardial space near the targeted myocardial tissue. Cooling of the myocardial tissue may also be accomplished by perfusing the target tissue with cooled solutions. Frequently, blood is taken from the angioplasty entry site (usually the groin), cooled outside the body, and then re-introduced into the patient, cooling the entire body. This approach is slow, due to requirements of cooling the whole body. In addition, the following re-elevation of the body temperature may require in excess of an hour. Cooling the blood requires a costly heat-exchanger, including the plumbing to transport blood from the patient to heat-exchanger and back. Cooling balloons present their own problems. Utilization of this cooling technology requires a cold flow of inflation media to the balloon and back. This is accomplished using complicated, multiple lumen catheter shafts. An external cold media is slowly pumped through the catheter at a predetermined flow rate, to the dilating pressure level. This is neither a simple nor low cost task. In addition, with perfusing balloons, the perfusion rate is often so high, that without a very large orifice to deliver the cold media, jetting of the media can occur and put the vessel at risk for further damage.

Direct injection of cold media often has little impact. Without the capability to hold the temperature at the desired target for an extended period, there is often no effect or benefit from the injection of cold media. Although injection of large amounts of cold media can extend the temperature reduction, this may lead to additional complications. When the flow of cold media is stopped, the arterial branch infused with the media may be shocked by the change. This can cause spasm or other reactions, and damage to the vessel.

SUMMARY

Overcoming the problems associated with cooling a local area leads to the requirements of a device that is preferably low-cost, easy to use, simple, capable of maintaining blood flow during the reduced temperature timeframe, capable of utilizing multiple types of cold media, low profile, and easy to manufacture.

In one aspect, a device for providing a fluid to a target tissue region of a body vessel is described. The device includes an elongate member having a lumen extending longitudinally therethrough from an entry port near a proximal end and to at least one exit port near a distal end of the elongate member, the member being adapted to receive a fluid into the entry port so that the fluid exits the at least one exit port and into a region of the vessel near a target tissue region. The device also includes a structure deployable from a distal portion of the elongate member, the deployable structure being adapted, when deployed, to channel blood flowing in the vessel and substantially isolate the blood flowing through the vessel from the region within the vessel near the target tissue region.

In another aspect, the device includes a structure deployable from a distal portion of the elongate member, the deployable structure being adapted, when deployed, to channel blood flowing in the vessel such that substantially all of the blood flowing through the vessel flows through the deployable structure. The device also includes an elongate member having a lumen extending longitudinally therethrough from an entry port near a proximal end and to at least one exit port near a distal end of the elongate member, the member being adapted to receive a fluid into the entry port so that the fluid exits the at least one exit port and into the interior of the deployable structure deployed in a vessel near a target tissue region.

In general, the distal end of the device is advancable through a body vessel to the target tissue region when the structure is in a non-deployed state. Likewise, the distal end of the device cannot be advanced through the body when the structure is in a deployed state. Usually, the proximal end of the elongate body remains outside the body when the distal end of the elongate body is positioned near the target tissue region.

The device may include a wire running from near the proximal end of the elongate member to a point of attachment to the structure, and wherein the structure is deployed from a distal portion of the elongate member by advancing the wire in a distal direction.

The device may include a wire loop and a blood channeler having a generally tubular shape. The wire loop includes a shape memory material. The blood channeler is adhesively bonded or welded to the wire loop. The blood channeler may be formed from nylon, PET, Pebax, POC, polyurethane, PTFE, or other biocompatible polymer. Alternatively, the blood channeler may include a mono-layer polymer material, or a layer of nano-laminates.

Variously, the fluid exits the lumen distally of the wire loop and outside the blood channeler, or the lumen extends distally of the wire loop and wraps around the outside of the deployable structure. The device may also include filter material attached to the outside of the distal end of the blood channeler, and lines attached to the filter material such that material collected by the filter material is retained by the filter material when the deployable structure is retracted. The lumen may have a perfusion section with multiple exit ports allowing fluid flow from the lumen into the blood channeled through the interior of the deployable structure.

Alternatively, the deployable structure may include an inflatable blood channeler. Fluid from the lumen may be able to pass into the inside of the inflatable blood channeler, and pass from the inside of the inflatable blood channeler into the blood being channeled through the deployable structure. The inflatable blood channeler may be made from nylon, PET, Pebax, POC, polyurethane, PTFE, or other biocompatible polymer. Alternatively, the deployable structure includes an expandable, non-inflatable material. The expandable, non-inflatable material may include a mono-layer polymer, or circumferential rings comprising a shape memory material. The shape memory material may be a polymer, or nitinol. The deployable structure may be self expanding, and may expand upon application of fluid pressure from the lumen, or upon application of cooled fluid from the lumen.

In another aspect, a method of providing a fluid to a target tissue region inside a body is described. The method includes introducing the distal end of a device as described above into a region of a body vessel near a target tissue region in a body vessel, deploying a deployable structure from a distal portion of the elongate member, and passing fluid through a lumen to at least one exit port located near the target tissue region.

The deployable structure may be adapted to channel blood flowing in a body vessel and substantially isolate the blood flowing through the vessel from the target tissue region, and wherein the fluid passes from the lumen such that the target tissue region substantially receives only the fluid provided through the lumen while blood continues to flow through the deployable structure and past the target tissue region. Alternatively, deployable structure may be adapted such that substantially all of the blood flowing through the vessel near the target tissue region flows through the deployable structure, and wherein the fluid passes from the lumen into the blood passing through the deployable structure near the target tissue region.

The deployable structure may include an inflatable balloon. The target tissue region may be located in a coronary artery. The method may include trapping material dislodged by the fluid such that the trapped material does not enter the body vessel blood flow. The fluid may be a cooled fluid, may include a drug, or may be a cooled fluid and the temperature at the target tissue region may be maintained for an extended period within a target temperature range.

In another aspect, a system for delivering fluid to a target tissue region inside the body is described including a device and structure such as described above, and a control system that controls the amount of fluid provided to the lumen and out of the exit port near the target tissue region. The system may deliver a fluid including a drug to the target tissue region, or may deliver cooled fluid to the target tissue region to maintain the target region at a temperature that is below normal internal human body temperature.

In another aspect, a process including diverting substantially all of the blood flowing through a body vessel from a target region inside a body such that the diverted blood does not exit the body, and infusing a fluid from outside a body to treat the target region is described.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 3 is a part longitudinal cross-section and part perspective view of a close up of the distal end of the local cooling device of FIG. 1 in a deployed state.

FIG. 4 is a cross-section of FIG. 3 taken along the cut-lines 4-4 in FIG. 3.

FIG. 5 is a perspective view of a distal end of one embodiment of a local cooling device.

FIG. 6 is a perspective view of a distal end of one embodiment of local cooling device.

FIG. 7 is a cross-sectional view of a portion of the cooling device of FIG. 6 near the distal end of the cooling device.

FIG. 8 is a perspective view of a distal end of one embodiment of local cooling device.

FIG. 9 is a perspective view of a distal end of one embodiment of local cooling device.

FIG 10 is a cross-section of FIG. 8 taken along the cut-lines 9-9 in FIG. 8.

Like reference symbols in the various drawings indicate like elements.

DETAILED DESCRIPTION

FIGS. 1, 2, 3, and 4 show one embodiment of a local cooling device 10. The local cooling device 10 may be inserted into and advanced to reach a target location 50 within the body, such as in a vessel 55.

Figure 1:
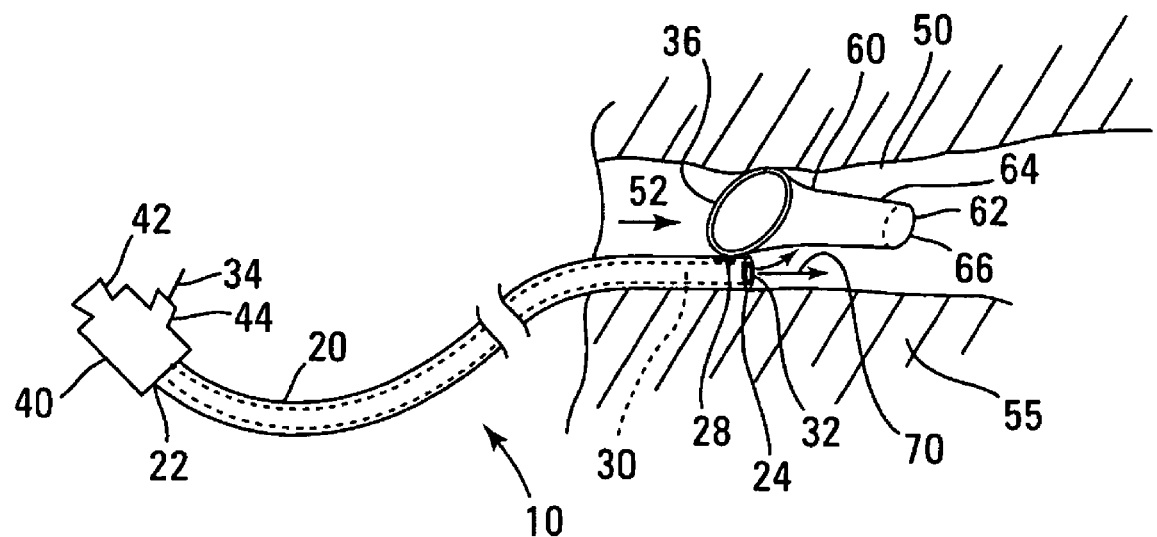
FIG. 1 is a side perspective view of one embodiment of a local cooling device, deployed in a vessel.

The local cooling device 10 includes an elongate shaft 20 and has a perfusion lumen 30 extending longitudinally therethrough. The perfusion lumen 30 extends from a proximal end 22 to a distal end 24 of the cooling device 10. An adapter 40 is attached to the proximal end 22 of the cooling device 10. Fluid 70 may be introduced into the perfusion lumen 30, pass through the perfusion lumen 30 and exit near the distal end 24 of the cooling device 10. The fluid 70 treats target location 50. A wire loop 36 and blood channeler 60 may be deployed from the cooling device 10 (as shown in FIG. 1) to divert blood flowing through the body vessel away from the target location 50.

This may be useful in various treatments. For example, a cooled fluid may be passed through the perfusion lumen 30 while the blood is diverted through the blood channeler 60. This allows the cooled fluid to remain localized for a longer period of time at the target location 50, enabling a more rapid, effective cooling of the target location 50, while decreasing the amount of cooled fluid that is required for cooling. In addition, the cooled fluid may be more concentrated at the target location 50 which may result in achieving lower temperatures and more localized cooling.

Referring again to FIG. 1, the cooling device 10 is shown deployed in a body vessel 55. The cooling device 10 has a proximal end 22, and an adapter 40 is attached to the proximal end 22 of the cooling device 10. The adapter 40 includes a fluid entry port 42 allowing the introduction of fluid and a wire access port 44 allowing the manipulation of a wire 34 to assist in deploying the wire loop 36 and blood channeler 60.

The cooling device 10 includes a wire 34 that runs from near the proximal end 22 to near the distal end 24 of the cooling device 10, and may also pass through and exit the adapter 40. In FIG. 1, the wire 34 is shown coming out of the wire access port 44 of the adapter 40. The wire 34 connects to the wire loop 36 located near the distal end 24 of the cooling device 10. The wire loop 36 is bonded to the blood channeler 60. The blood channeler 60 has a proximal end formed by the wire loop 36, and a distal end 62. The wire loop 36 controls the diameter size of the proximal end of the blood channeler 60. When deployed in a body vessel 55, such as a coronary artery, the wire loop 36 of the cooling device 10 expands to just slightly smaller than the diameter of the body vessel 55 in front of the target location 50. Thus, the blood channeler 60, having a generally tubular construction, has a diameter at the proximal or blood entry end just slightly smaller than the internal diameter of the body vessel in which it is deployed. The blood channeler 60 also has a reduced, or necked, area 64, and an exit port 66, located at the distal end 62 of the blood channeler 60. When the wire loop 36 and blood channeler 60 are fully deployed, blood 52 flowing through the body vessel enters the proximal end of the blood channeler 60 formed by the wire loop 36. This diverts the majority of the blood moving through the body vessel 55 from a target location 50 by passage through the blood channeler 60. The blood travels through the blood channeler 60, through the narrowest part, the neck 64 of the blood channeler 60, and then exits through the exit port 66 at the distal end 62 of the blood channeler 60.

Fluid may be introduced by passing fluid through the fluid entry port 42 and into the perfusion lumen 30 at the proximal end 22 of the cooling device 10. The fluid travels through the perfusion lumen 30, and exits via the fluid exit port 32 near the distal end 24 of the cooling device 10. The fluid exit port 32 is located distal of the wire loop 36 and the proximal edge of the blood channeler 60 formed by the wire loop 36. The fluid exit port 32 and is between the outside of the blood channeler 60 and the walls of the body vessel 55. When properly deployed, the fluid 70 exits the cooling device 10 near target location 50. The cooling fluid 70 circulates around the outside of the blood channeler 60, and cools the target area 50 in the body vessel 55. The cooling fluid 70 stays at the target location 50 for a period of time due to the lack of flow, as the blood 52 is flowing through the inside of the blood channeler 60. Near the distal end 62 of the blood channeler 60, the cooling fluid 70 and the blood 52 mix. Thus, the deployed blood channeler 60 diverts most, if not all, of the blood 52 from the target location 50, allowing the cooling fluid 70 to treat the target area 50.

When undeployed, the wire loop 36 and blood channeler 60 are stored in a device lumen 38 located near the distal end of the shaft 20. The wire 34 may be advanced or pushed to deploy the wire loop 36 and blood channeler 60 from the device lumen 38 near the distal end 24 of the cooling device 10. The device lumen 38 has a device exit port 28 at the distal end of the device lumen 34, where the wire loop 36 and blood channeler 60 may exit the shaft 20. The device lumen 38 may extend longitundinally from the proximal end 22 to near the distal end 24 of the cooling device 10. Alternatively, the device lumen 38 may only extend a short distance to near the distal end 24 of the cooling device. The device lumen 38 is large enough to allow storage of the wire loop 36 and blood channeler 60 before deployment, and allow retraction of the wire loop 36 and blood channeler 60 after treatment has completed.

The local cooling device 10 may be advanced to a target location 50 by inserting the cooling device 10 into the body via a vessel, such as an artery, and then advanced to the target location 50. Alternatively, the cooling device 10 could be advanced over a guidewire (not shown) which may be used to guide the cooling device 10 to the target location 50. After the cooling device 10 reaches the target location, the guidewire may be removed from the body vessel and the body. When using a guidewire, the perfusion lumen 30 may be used as a lumen for passage of the guidewire.

Figure 2:
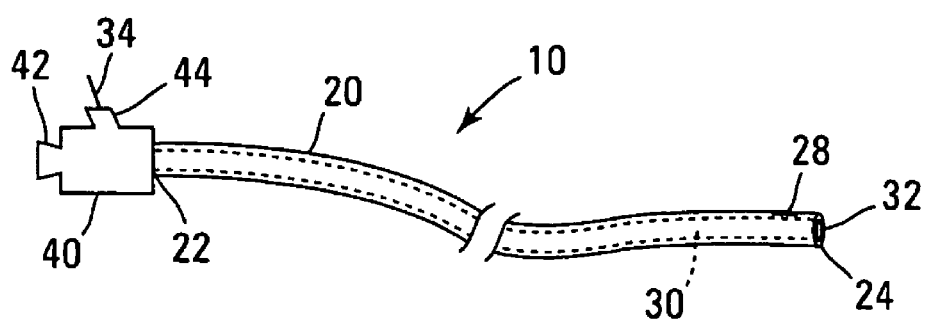
FIG. 2 is a side perspective view of one embodiment of a local cooling device, shown undeployed.

FIG. 2 shows a side perspective of the cooling device 10 of FIG. 1 in an undeployed state. The wire loop 36 and blood channeler 60 are within the device lumen 38 (all not shown in FIG. 2), and may be deployed via device exit port 28 by operation of the wire 34.

FIG. 3 shows a more detailed view of the portion of the cooling device 10 near the distal end 24 of the cooling device 10. The wire loop 36 and blood channeler 60 are shown in a deployed state. As can be seen, the wire 34 is operably connected to wire loop 36, and can be used to advance the wire loop 36 and blood channeler 60 from the device lumen 38 and out of the device exit port 28. The wire 34 may also be used to retract the wire loop 36 and blood channeler 60 back into the device lumen 38 via the device exit port 28. A distal portion of the lumen thus serves as a storage area for the deployable blood channeler 60.

FIG. 4 shows a cross section of the shaft 20, taken along cut lines 4-4 in FIG. 3. This cross section shows the perfusion lumen 30 and the device lumen 38, both formed by the shaft 20. Wire 34 runs through the device lumen 38.

Another embodiment of a local cooling device 110 in accordance with the invention is shown in FIG. 5, which is a perspective view of the cooling device 110 near the distal end 124 of the cooling device 110. The cooling device includes an elongate shaft 120, and has a proximal end (not shown) and a distal end 124. A perfusion lumen (not shown) is formed by the shaft 120, and has a fluid exit port 132 at the distal end 124 of the cooling device.

A wire (not shown) runs the length of the shaft and is operably connected to a wire loop 136. The wire loop 136 is bonded to a blood channeler 160. The wire loop 136 forms the proximal end of the blood channeler 160. The blood channeler 160 also has narrow neck portion 164, and a distal end 162. An exit port 166 is located at the distal end 162 of the blood channeler 160.

A filter material 180 is bonded to the outside of the distal end 162 of the blood channeler 160. The filter material 180 extends outward from the blood channeler 160, and contacts the walls in the body vessel when deployed. The filter material 180 may be made of filter mesh formed from a polymer or other material. A number of traces 182 are bonded or connected to the wire loop 136 periodically around the circumference of the wire loop 136. These traces 182 run from the wire loop 136 to a point at which the traces 182 bond or connect to the filter material 180. Thus, there are a number of places around the circumference of the wire loop 136 of the local cooling device 110 at which the traces 180 are bonded or connected to filter material 180. The traces 182 may be formed of a material, such as a shape memory material, that assists in maintaining the filter material 180 deployed.

When deployed, the wire loop 136 will contact the walls of the body vessel 155, and blood 150 flowing through the body vessel 155 will be diverted through the blood channeler 160. When fluid 170 is passed through the perfusion lumen (not shown) and out of the fluid exit port 132, the fluid 170 will treat target location 150. During treatment, some material may be dislodged from the target location 150. For example, the cooling may dislodge blood clots, cholesterol pieces, or bits of plaque. The deployed filter material 180 will catch and retain particles or dislodged material larger than the pore size of the filter material 180, and not allow those particles to proceed further in the bloodstream.

After treatment, when the wire loop 136 and blood channeler 160 are retracted into the device lumen (not shown) of the local cooling device 110, the filter material 180 and traces 182 will also be retracted. These components may be retracted into the local cooling device in such a way that the filter material 180 and traces 182 interact to close the filter material 180 as it retracts. Thus, any particles or material captured in the filter material 180 would not be dislodged into the blood stream, but would be kept in the filter material 180 by operation of the traces 182. Thus, the dislodged material will also be retracted into the device lumen and removed from the body when the local cooling device 110 is removed from the body.

In another embodiment, the area between the traces may also partly or fully include a filter material. This would enable the use of solid particles, such as small ice particles, to be passed through the perfusion lumen and used for localized cooling. The enclosing filter would retain these ice particles until they are less than a determined size. This would enable more rapid cooling.

Another embodiment of a local cooling device 110 in accordance with the invention is shown in FIGS. 6 and 7. FIG. 6 is a perspective view of the cooling device 210 near the distal end 224 of the cooling device 210. The cooling device includes an elongate shaft 220, and has a proximal end (not shown) and a distal end 224. A perfusion lumen (not shown) is formed by the shaft 220, and runs throughout the shaft 220 from the proximal end of the cooling device 210 to near the distal end 224. The perfusion lumen is connected to a perfusion sheath 231.

A wire 234 is operably connected to a wire loop 236. A blood channeler 260 is bonded to the wire loop 236. The blood channeler 260 has a proximal end formed by the wire loop 236, a reduce area 264 located at about the midpoint of the blood channeler 260, and a distal end 262. A device exit port 232 is located at the distal end 262 of the blood channeler 260.

The cooling device 210 is shown in a deployed state in FIG. 6. The perfusion sheath 231 is wrapped in a spiral manner around the outside of the blood channeler 260. The perfusion sheath 231 has numerous perfusion exit ports 233 located along its length. The perfusion exit ports 233 point outward from the blood channeler 260. When fluid is perfused through a device in the body, there is a risk of perfusion injury due to the flow of the fluid. The numerous perfusion exit ports 233 in the perfusion sheath 231 reduce the risk of injury, as the fluid is perfused through numerous perfusion exit ports 233. The sum of the areas of the perfusion exit ports 233 exceeds the area of the device exit port 232. Preferably, the sum of the areas of the perfusion exit ports 233 will be at least twice the area of the device exit port 232.

When undeployed, the wire loop 236, blood channeler 260, and perfusion sheath 231 reside within the cooling device 210 near the distal end 224. When deployed, the wire 234 may be advanced, which advances the wire loop 236, blood channeler 260, and perfusion sheath 231 out of the device exit port 232 located at the distal end 224 of the cooling device 210. After treatment is complete, the wire 234 may be retracted, which in turn, retracts the wire loop 236, blood channeler 260, and perfusion sheath 231.

FIG. 7 is a cross-sectional view of a portion of the cooling device of FIG. 6 near the distal end of the cooling device. This view shows a perfusion lumen 230 and a device lumen 238 formed by the shaft 220 of the cooling device 210. The wire 234 extends through the device lumen 238 and is connected with the wire loop 236. The perfusion sheath 231 is shown attached to the interior of the shaft 220, and exits the cooling device 210 via the device exit port 232, before wrapping around the blood channeler 260. Fluid is able to flow through the perfusion lumen 230 and into the perfusion sheath 231. When not deployed, the wire loop 236, perfusion sheath 231, and blood channeler 260 are stored in the distal end of the cooling device 210. The wire loop 236, perfusion sheath 231, and blood channeler 260 are deployed by advancing through the device exit port 232, and undeployed by retracting through the device exit port 232. A distal portion of the device inside the shaft 220 thus serves as a storage area for the deployable blood channeler 260.

One concern with the application of cooling fluids into body vessels is the possibility of damage to the body vessel caused by jetting. As the fluids exit into the body vessel from a delivery device, there is the possibility that the fluid will damage the body vessel due to the flow rate of the cooling fluid. The following embodiments address this potential issue by perfusing from the outside in. The walls of the body vessel are protected by a layer of material of the delivery device.

An embodiment of a local cooling device 310 in accordance with the invention, shown in FIG. 8, includes an elongate shaft 320 having a proximal end (not shown) and a distal end 322. The shaft 320 has a perfusion lumen (not shown) formed by the shaft 320. The perfusion lumen extends from an entry port (not shown) near the proximal end of the cooling device 310 to a series of exit ports 326, near the distal end 322 of the shaft 320.

The local cooling device 310 also includes a blood channeler 360. The blood channeler 360 includes ribs 362 and a material portion 364. The ribs 362 may be formed from a shape memory material, such as nitinol, or other material. The ribs 362 are connected to the sheath material 364, for example by bonding.

When fully deployed, the ribs 362 form a generally spiral configuration, with the ribs 362 and sheath material 364 between the ribs forming a tunnel for blood to flow through. The leading edge of the ribs 362 forms the proximal end of the blood channeler 360, while the distal end of the blood channeler 360 is formed by the trailing edge of the ribs 362. The ribs 362 control the diameter size of the blood channeler 360. The deployed blood channeler 360 deploys to fill the body vessel in which it is deployed, and the blood channeler 360 may touch the vessel walls. The blood channeler 360 may be self-expanding. Alternatively, a wire may be operably connected to the ribs 362, and advancing the wire may deploy the blood channeler 360.

Before deployment, the blood channeler 360 including ribs 362 and sheath material 364 may be partially stored within a device lumen (not shown), and partially wrapped around the outside of the cooling device 310 near the distal end 322 of the cooling device 310. During deployment, some of the ribs 362 and sheath material 364 is advanced from the device lumen out the device exit port 368. The blood channeler 360 may deploy by taking advantage of properties of the shape change material. For example, the associated shape change may occur under pressure or temperature change. Alternatively, the blood channeler may deploy by advancing a wire connected to the ribs 362.

The cooling device 310 in FIG. 8 is shown expanded and deployed. The ribs 362 of the cooling device 310 are expanded forming a tunnel. Blood flowing through a body vessel in which the cooling device is deployed enters the proximal end of the blood channeler 360. At the same time, a cooling fluid 370 is passed through a perfusion lumen and exits at perfusion exit ports 326. Therefore, as blood travels through the blood channeler 360, it mixes with the cooling fluid 370, causing the blood to cool before it exits the distal end of the blood channeler 360.

The body vessel 350 is protected as the cooling fluid 370 perfuses through the exit ports 326 towards the middle of the vessel. Thus, the cooling fluid 370 interacts with the blood in the space formed by the blood channeler 360. In addition, the walls of the vessel are protected by the blood channeler 360. Therefore, the blood channeler 360 protects the walls of the body vessel, as fluid 370 will strike the blood channeler 360 and not the walls of the body vessel.

The fluid used with any of the devices of this invention may be blood, saline solution, or another suitable fluid. The fluid may be cooled. The fluid may be oxygenated. The cooled fluid may include particles, such as ice crystals to enhance cooling. The fluid may include drugs, such as an anti-inflammatory, anti-coagulant, or other drug(s) to assist in treating the patient.

The blood channeler may be formed, for example, of nylon, pebax, POC, PET, ePTFE, urethane, polymer blends, other polymers, or other material. The sheath may be formed of a mono-layer or a multi-layer material. As the inner blood flow and outer cooling fluid flow do not mix until near the distal end of the sheath, there is minimal heat exchange between the fluids over the length of the sheath.

In order to further decrease heat conductivity across the blood channeler, nano-laminates of dissimilar materials may be applied to the blood channeler. This would act to maintain maximum cooling of the target area, as heat transfer to the flowing blood on the other side of the sheath would be further minimized. It has been found recently that heat cannot be carried efficiently across these material interfaces. Heat is transferred normally by lattice vibrations. When using dissimilar materials, an amount of these lattice vibrations are merely reflected instead of transferred through the material. By making the individual layers only a few nanometers thick, a nanolaminate material with a thermal conductivity three times less than a conventional insulator has been produced. The deposition of single molecule layers of dissimilar materials on top of a base polymeric sheath may be achieved using a polyelectrolyte method.

Another embodiment of a local cooling device 410 in accordance with the invention is shown in FIGS. 9 and 10. FIG. 9 is a perspective view of the area near the distal end of the cooling device 410. FIG. 10 is a cross section of a portion of the cooling device 410 in the area of the expandable sheath 460, taken along cut lines 10-10 in FIG. 9.

The cooling device 410 includes an elongate shaft 420 having a proximal end (not shown) and a distal end 422. A perfusion lumen 430 is formed by the shaft 420 and extends longitudinally through the shaft 420 to near the distal end 424. The perfusion lumen 430 extends from an entry port (not shown) to an expandable sheath 460 located near the distal end 424 of the cooling device 410.

The cooling device 410 is shown expanded and deployed in FIG. 9. Before deployment, the expandable sheath 460 may be wrapped and folded around the shaft 420 in the area near the distal end 424 of the cooling device 410.

The expandable sheath 460 may be deployed by injecting a fluid 470 into the perfusion lumen 430 and passing the fluid 470 through the perfusion lumen 430 into the interior of the expandable sheath 460. The fluid 470 may enter the expandable sheath 460 via perfusion exit ports 472 that lead from the perfusion lumen 430 into the interior of the expandable sheath 460. The expandable sheath 460 expands and deploys as fluid is passed into the interior of the expandable sheath 460. The expandable sheath 460 expands to the diameter of a body vessel 450 in which it is located. The expandable sheath is placed just prior to a target location 480 in the body. The expanded sheath has a proximal end 462 and a distal end 464. As blood 452 travels along the body vessel 450, it enters the proximal end 462 of the expandable sheath 460.

As fluid 470 is passed through the perfusion lumen 430, and expanding the expandable sheath 460, some of the fluid 470 also passes through fluid exit ports 426. Fluid exit ports 426 are located on the interior surface of the expandable sheath 460, and also the interior surface of the shaft 420 located within tunnel formed by the expandable sheath 460. These exit ports 426 may be located in perfusion strips forming parts of the sheath, or may be exit ports located as part of the inner surface of the expandable sheath 460. There may be one or more exit ports 426.

Exit port 426 are located along the shaft 420, and also exit ports 426 along the inner edge of the balloon directly across from the shaft 420, and exit ports 426 on the inner wall on each side halfway between the other described sets of exit ports 426. This is more clearly shown in FIG. 10. Fluid 470 passes out of the perfusion lumen 430 and into the expandable sheath 460. Fluid 470 also exits through fluid exit ports 426 located at 0°, 90°, 180°, and 270° around the inside of the expandable balloon 460 in this embodiment as shown in FIG. 10.

As the fluid 470 exits towards the interior of the expandable sheath 460, the walls of the body vessel 450 are protected from jetting damage. The fluid 470 perfuses through the exit ports 426 towards the middle of the vessel, rather than from the middle towards the walls of the body vessel 450. Thus, the fluid 470 interacts with the blood 452 in the space formed by the expandable sheath 460, and would strike the inner wall of the sheath 460 and not the walls of the body vessel 450. As blood 452 passes through the proximal end 442 of the expandable sheath 460, and through the expandable sheath 460, fluid 470 mixes with the blood 452. When a cooled fluid is used, this mixing causes the blood to cool before it exits the distal end 444 of the expandable sheath 460.

The fluid exit ports 426 may be constructed to only allow passage of fluid at a certain pressure or higher. This design enables the expandable sheath 460 to be fully expanded and remain expanded, while fluid 470 is being perfused out of the fluid exit ports 426. The fluid exit ports 426 may be designed to only allow one direction of fluid flow. Thus, only fluid flowing form the cooling device 410 into the body vessel would be allowed. In such a design, blood 452 could not enter or flow into the cooling device 410. The uni-directional fluid exit ports would also allow the expandable sheath 460 to be retracted after treatment is completed. Instead of perfusing fluid, a slight vacuum could be pulle don't eh perfusion lumen 430. This would evacuate all the fluid from the expandable sheath 460, and bring the sheath down to where it is closely wrapped on the shaft 420 near the distal end 424 of the cooling device 410. This would enable the cooling device 410 to be removed form the patient following treatment.

The expandable sheath may be formed, for example, of nylon, pebax, POC, PET, ePTFE, urethane, polymer blends, other polymers, or other material. The sheath may be formed of a mono-layer or a multi-layer material.

Figure 11:
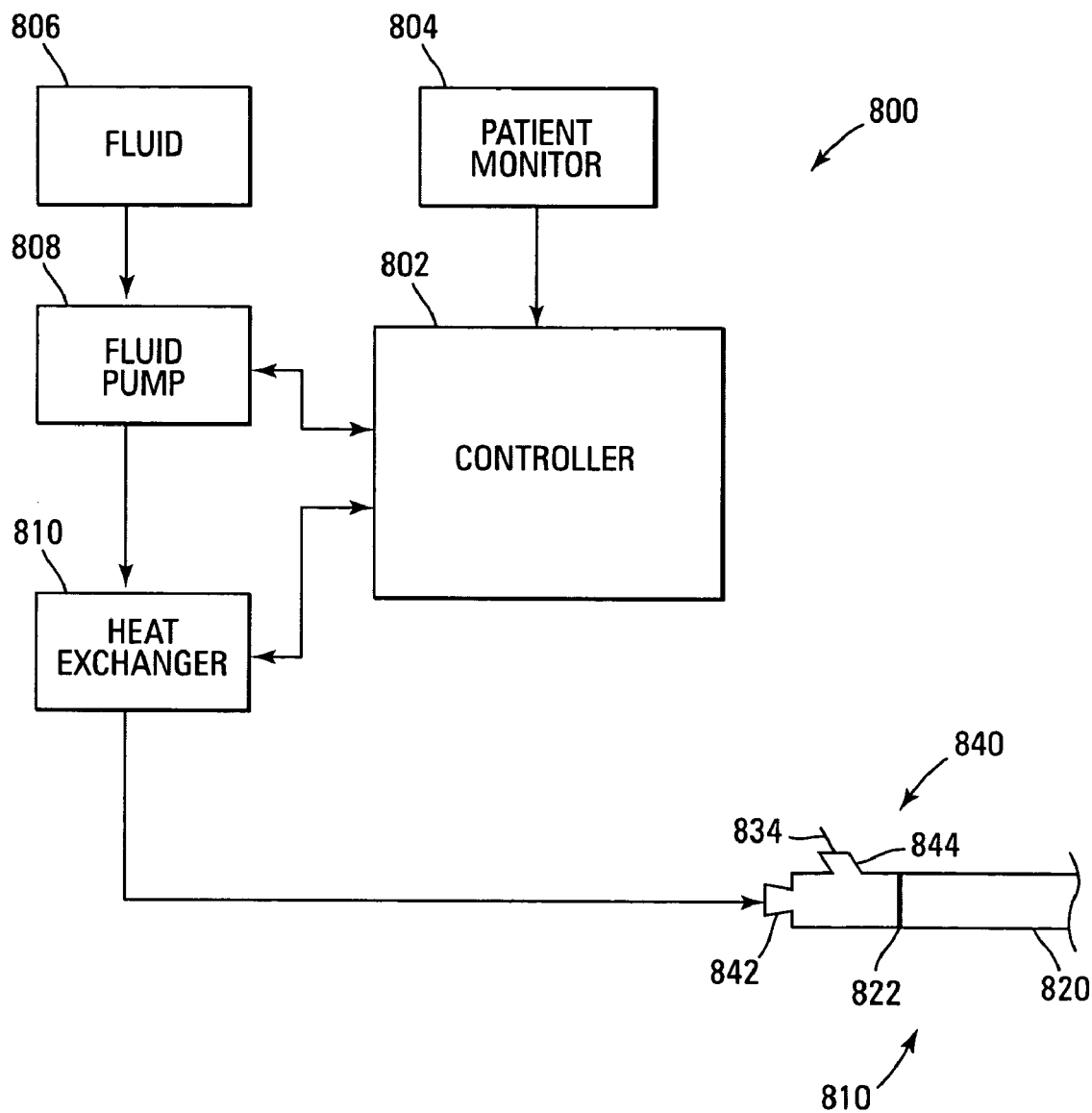
FIG. 11 is a diagram of a side view of a proximal end of a local cooling device used to cool a target tissue region and a control system connected to the proximal end of the local cooling device, the control system shown in block diagram.

FIG. 11 shows a system including a local cooling device 810 (only a portion of which is shown) and external equipment attached to the local cooling device 810. In this example, the proximal end 822 of the shaft 820 of the local cooling device 810 is attached to an adapter 840. The adapter 840 includes a fluid access port 842 and a wire access port 844. A wire 834 is shown coming out of the wire access port 844.

A control system 800 is shown in box diagram, and includes a controller 802, a patient monitor 804, a fluid reservoir 806, a fluid pump 808, and a heat exchanger 810. The controller 802 receives information from the patient monitor 804 and uses that information to control the amount and temperature of the fluid delivers to the local cooling device 820 by controlling the operation of the fluid pump 808 and the heat exchanger 810.

Fluid access port 842 on the adapter 840 provides access to a perfusion lumen (not shown) that extends longitudinally through the shaft 820 of the local cooling device 810 to near the distal end (not shown) of the cooling device 810. The fluid pump 808 is connected to the perfusion lumen via port 842. The controller 802 controls the operation of the fluid pump 808, and the amount and rate of cooled fluid provided to local cooling device 820. The fluid provided to the local cooling device 820 may be blood, saline solution, or another suitable fluid. The fluid may be cooled. The fluid may include pharmaceutical drugs or other materials.

The port 844 provides access to a device lumen that extends longitudinally through the shaft 820 of the local cooling device 810 to near the distal end of the cooling device 810. A wire 834 runs from outside the body, via port 844, and in some embodiments, may be manipulated to deploy and retract the deployable portion of the local cooling device 810. Typically, the wire 834 may be advanced, retracted, and rotated to assist in operating the local cooling device most effectively and efficiently.

In other implementations, additional external devices may be added to the control system 800, or alternatively, some of the devices may be omitted.

The local cooling device may be used to cool tissue regions in all areas of the body. For example, the local cooling device may be used near the heart or aorta, near the brain, kidneys, and in the legs, torso, or arms.

A number of embodiments of the invention have been described. Nevertheless, it will be understood that various modifications may be made without departing from the spirit and scope of the invention. Accordingly, other embodiments are within the scope of the following claims.

What is claimed is:

1. A device for providing a fluid to a target tissue region of a body vessel, the device comprising:
   an elongate member having a lumen extending longitudinally therethrough from an entry port near a proximal end and to at least one exit port near a distal end of the elongate member, the member being adapted to receive a fluid into the entry port so that the fluid exits the at least one exit port and into a region of the vessel near a target tissue region; and
   a structure deployable from a distal portion of the elongate member, the deployable structure being adapted, when deployed, to channel blood flowing in the vessel and substantially isolate the blood flowing through the vessel from the region within the vessel near the target tissue region.

2. The device of claim 1, wherein the distal end of the device is advancable through a body vessel to the target tissue region when the structure is in a non-deployed state.

3. The device of claim 2, wherein the distal end of the device cannot be advanced through the body when the structure is in a deployed state.

4. The device of claim 1, wherein the proximal end of the elongate body remains outside the body when the distal end of the elongate body is positioned near the target tissue region.

5. The device of claim 1, further comprising a wire running from near the proximal end of the elongate member to a point of attachment to the structure, and wherein the structure is deployed from a distal portion of the elongate member by advancing the wire in a distal direction.

6. The device of claim 1, wherein the structure comprises a wire loop and a blood channeler having a generally tubular shape.

7. The device of claim 6, wherein the wire loop comprises a shape memory material.

8. The device of claim 6, wherein the blood channeler is adhesively bonded or welded to the wire loop.

9. The device of claim 6, wherein the blood channeler is formed from nylon, PET, Pebax, POC, polyurethane, PTFE, or other biocompatible polymer.

10. The device of claim 9, wherein the blood channeler comprises a mono-layer polymer material.

11. The device of claim 6, wherein the blood channeler comprises a layer of nano-laminates.

12. The device of claim 6, wherein the fluid exits the lumen distally of the wire loop and outside the blood channeler.

13. The device of claim 6, further comprising:
   filter material attached to the outside of the distal end of the blood channeler; and
   lines attached to the filter material such that material collected by the filter material is retained by the filter material when the deployable structure is retracted.

14. The device of claim 1, wherein the structure comprises a proximal mouth and a distal mouth, wherein the structure is deployable so that the proximal mouth is proximal the at least one exit port and the distal mouth is distal the at least one exit port.

15. The device of claim 1 wherein the at least one exit port is outside the structure when the deployable structure is deployed.

16. The device of claim 5, wherein the elongate member further comprises a second lumen extending from a proximal opening to a distal opening, wherein the wire is at least partially disposed within the proximal opening.

17. The device of claim 16 wherein the distal opening is proximal the at least one exit port.

18. The device of claim 16 wherein the distal opening is a lateral opening near the distal end of the elongate member.

19. The device of claim 6, wherein the blood channeler has a necked portion.

* * * * *

UNITED STATES PATENT AND TRADEMARK OFFICE
CERTIFICATE OF CORRECTION

| | | |
|---|---|---|
| PATENT NO. | : 7,963,940 B2 | Page 1 of 1 |
| APPLICATION NO. | : 11/208879 | |
| DATED | : June 21, 2011 | |
| INVENTOR(S) | : Thomas J. Holman et al. | |

It is certified that error appears in the above-identified patent and that said Letters Patent is hereby corrected as shown below:

Column 10
Line 53, delete "...pulle don't eh...", and insert therefor -- pulled on the --.

Signed and Sealed this
Twenty-third Day of August, 2011

David J. Kappos
*Director of the United States Patent and Trademark Office*